United States Patent
Bachman et al.

(10) Patent No.: US 6,764,999 B2
(45) Date of Patent: Jul. 20, 2004

(54) NASAL DELIVERY OF PARASITICIDES

(76) Inventors: Stephen E. Bachman, 682 Glenoak La., Amarillo, TX (US) 79109; Michael E. Hubbert, 74C Rim Rd., Arroyo Seco, NM (US) 87514

( * ) Notice: Subject to any disclaimer, the term of this patent is extended or adjusted under 35 U.S.C. 154(b) by 0 days.

(21) Appl. No.: 10/194,845

(22) Filed: Jul. 11, 2002

(65) Prior Publication Data

US 2004/0009929 A1 Jan. 15, 2004

(51) Int. Cl.[7] .................. A01N 43/04; A61K 31/70; A61F 13/00

(52) U.S. Cl. ............... 514/30; 514/29; 424/434

(58) Field of Search .......................... 514/30

(56) References Cited

U.S. PATENT DOCUMENTS

| | | | |
|---|---|---|---|
| 3,950,360 A | 4/1976 | Aoki et al. ............. 260/343.2 |
| 4,173,571 A | 11/1979 | Chabala et al. ........ 260/343.41 |
| 4,199,569 A | 4/1980 | Chabala et al. ............ 424/180 |
| 4,201,861 A | 5/1980 | Mrozik et al. ............. 536/17 A |
| 4,206,205 A | 6/1980 | Mrozik et al. ............. 424/180 |
| 4,310,519 A | 1/1982 | Albers-Schonberg et al. ............. 424/181 |
| 4,612,186 A | * 9/1986 | Eckenhoff et al. ....... 604/892.1 |
| 4,853,372 A | * 8/1989 | Williams et al. |
| 5,116,968 A | * 5/1992 | Lawrence et al. |
| 5,728,719 A | * 3/1998 | Miller ..................... 514/360 |
| 5,731,303 A | * 3/1998 | Hsieh |
| 5,733,566 A | * 3/1998 | Lewis ..................... 424/426 |
| 2002/0107265 A1 | * 8/2002 | Chen et al. ................. 514/310 |

OTHER PUBLICATIONS

"Comparison of Pharamacokinetic Profiles of Doramectin . . . ", Gayrard, et al., 1999, pp. 47–55.

"Comparing Pharamacokinetics of IVOMEC", Bicknese, 1994, pp. 13–17.

* cited by examiner

*Primary Examiner*—Traviss C. McIntosh, III
(74) *Attorney, Agent, or Firm*—Dale F. Regelman

(57) ABSTRACT

A method to treat an animal in need thereof with one or more parasiticides by administering those one or more parasiticides to the nasal pharynx of the animal. A method to increase an animal's blood levels of one or more avermectin compounds/milbemycin compounds such that the blood levels of those one or more avermectin compounds/milbemycin compounds reach a maximum concentration in about 24 hours, and such that those blood levels exceed about 2 ng/ml for at least 96 hours post administration.

13 Claims, 1 Drawing Sheet

NASAL DELIVERY OF PARASITICIDES

FIELD OF THE INVENTION

The present invention relates to a method to increase blood levels of one or more parasiticides by administering those one or parasiticides to the nasal pharynx of animals, including humans. In certain embodiments, Applicants' invention relates to a method to increase blood levels of one or more macrocyclic lactone parasiticides by administering those one or macrocyclic lactone parasiticides to the nasal pharynx of animals, including humans. In certain embodiments, Applicants' invention relates to a method to increase blood levels of ivermectin by administering ivermectin to the nasal pharynx of animals, including humans.

BACKGROUND OF THE INVENTION

The avermectin family, of which ivermectin is a member, is a series of very potent antiparasitic agents which are useful against a broad spectrum of endoparasites and ectoparasites in mammals. Ivermectin is disclosed in U.S. Pat. No. 4,199,569, issued Apr. 22, 1980 to Chabala and Fisher. Ivermectin is a mixture, in the ratio of approximately 80:20 of 22,23-dihydro C-076 B1a and B1b.

Ivermectin is a member of a family of compounds identified as avermectins. The basic avermectin compounds are isolated from the fermentation broth of the microorganism *Streptomyces avermitilis*. Such compounds are described in U.S. Pat. No. 4,310,519. In addition, certain derivatives of these basic fermentation products have been prepared. Some of the avermectins contain a 22,23-double bond. This may be selectively reduced to prepare the ivermectin compounds discussed above. In addition, the avermectins possess a disaccharide moiety at the 13-position consisting of the a-L-oleandrosyl-a-L-oleandrosyl group. One or both of these saccharide groups may be removed as described in U.S. Pat. No. 4,206,205. The thus produced aglycone derivatives have a hydroxy group at the 13-position. This group may be removed to form the 13-deoxy compound as described in U.S. Pat. Nos. 4,171,314 and 4,173,571. On the avermectin compounds and derivatives are several hydroxy groups which may be acylated as described in U.S. Pat. No. 4,201,861.

A series of compounds identified as milbemycin compounds have the same 16 membered macrocyclic ring as do the avermectin compounds, although they do not have the disaccharide moiety and also differ in the nature of other substituent groups. These compounds are disclosed in U.S. Pat. No. 3,950,360 and they also would be expected to benefit in their spectrum of activity by the instant process and formulations.

Various medicaments, including avermectin compounds/milbemycin compounds, have traditionally been administered orally or by injection (subcutaneous, intramuscular) to animals, including humans. In the context of feedstock animals, i.e. meat-producing animals, such avermectin compounds/milbemycin compounds are sometimes added to the animals' food. Such oral administration, however, does not effectively deliver the proper dosage to each and every animal. Significantly, animals that are sick often do not eat or drink properly. These sick animals, however, may be in greatest need such medicaments, including one or more avermectin compounds/milbemycin compounds.

Administration of avermectin compounds/milbemycin compounds to feedstock animals via intramuscular injection is an effective, but undesirable route of dosing. This route requires sterile procedures that can be difficult to maintain under field conditions. Intramuscular injections often result in tissue bruising, injection site lesions and concomitant product loss post-mortem.

Subcutaneous injection can be difficult to administer and can cause swelling at the injection site. Furthermore, subcutaneous injections may be given intramuscularly by mistake and reduce the effectiveness of the active compound. Animals/humans do not like injections and can move during the administration causing the needle to break off at the injection site. This creates a hazard for the animal/human and a contaminant in the food chain.

What is needed is a method to administer one or more parasiticides to animals, including humans, where that method is both cost-effective and time-effective.

SUMMARY OF THE INVENTION

Applicants' invention includes a method to treat an animal in need thereof with one or more parasiticides by administering those one or more parasiticides to the nasal pharynx of the animal. Applicants' invention further includes a method to increase blood levels of one or more avermectin compounds/milbemycin compounds such that the blood levels of those one or more avermectin compounds/milbemycin compounds reach a maximum concentration in about 24 hours, and such that those blood levels exceed about 2 ng/ml for at least 96 hours post administration.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
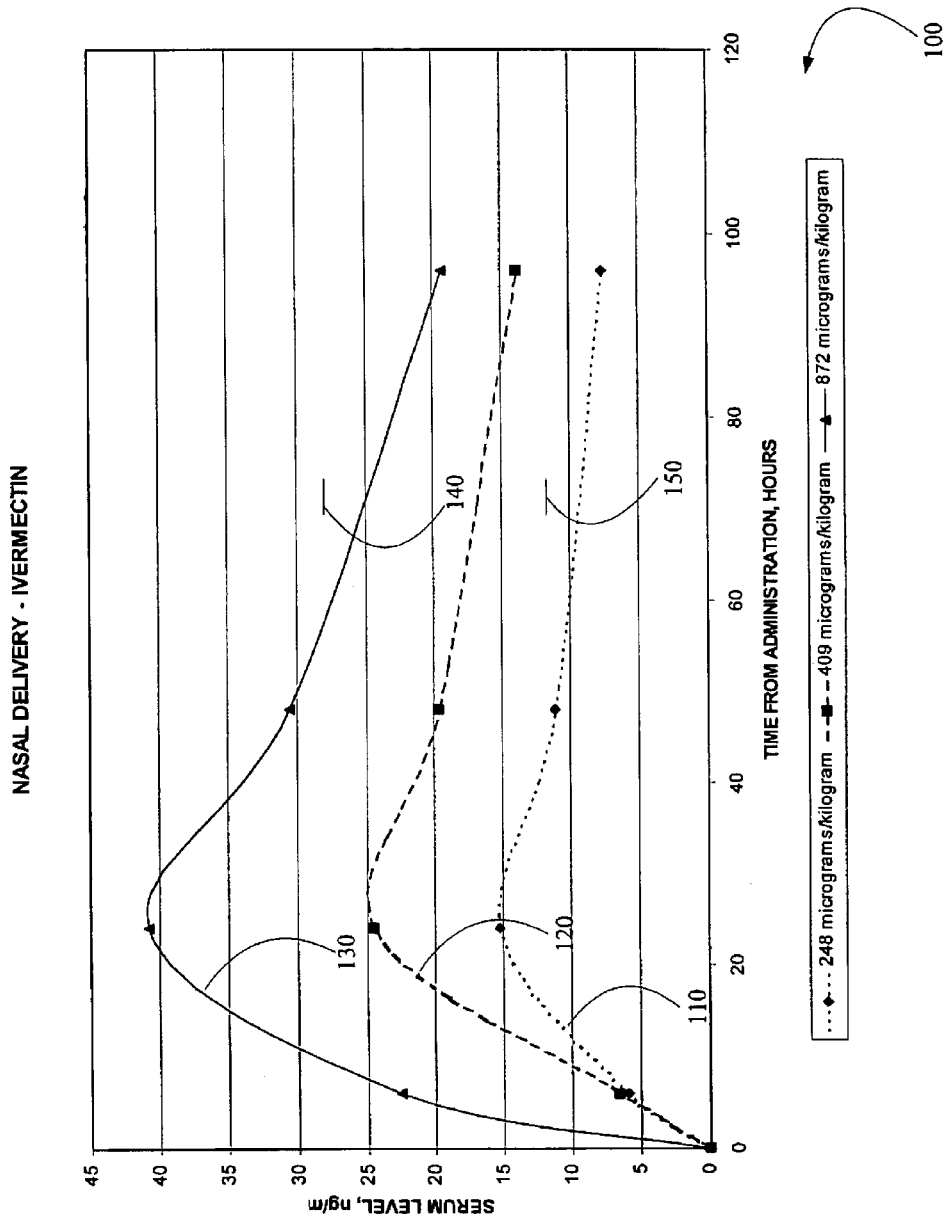
FIG. 1 is a graph showing serum levels of ivermectin as a function of time after administering the ivermectin to the nasal pharynx.

Applicants' invention will be described as embodied in a method to increase serum levels of ivermectin in feedstock animals. The following description of Applicant's nasal delivery method is not meant, however, to limit Applicant's invention to administering ivermectin to meat-producing animals, as the invention herein can be applied generally to administering one or more avermectin compounds/milbemycin compounds to animals, including humans.

The macrocyclic lactones are natural fermentation products of soil-dwelling Streptomycetes bacteria. They consist of two sub groups, the avermectins and the milbemycins. Their basic chemical structure consists of a macrocyclic lactone, a spiroketal addition fused from C-17 to C-25 and a hexahydrobenzofiran unit fused from C-2 to C-8. The avermectins also include an oxy disaccharide substituted at position C-13 whereas this position is not substituted in the milbemycins. Several different alkyl groups can be substituted at position C-25 in both sub groups. The basic structures of the two can be superimposed on each other. As a result the avermectins may be described as glycosylated milbemycins. Conversely the milbemycins may be described as deglycosylated avermectins.

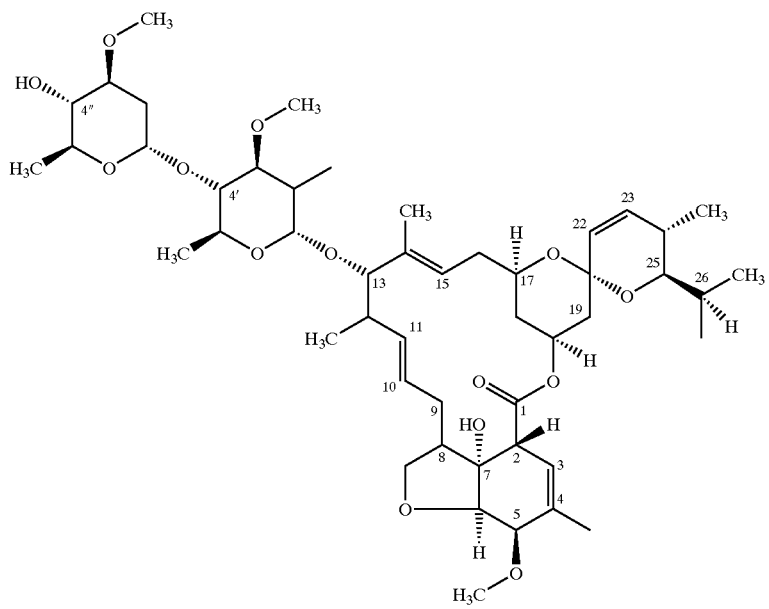

The macrocyclic lactones have broad spectrum activities against a wide range of nematodes and arthropods and their effectiveness against both endo- and ectoparasites has given rise to the name endectocides. They are highly effective at low doses (micrograms per kilogram of body weight) against most of the economically important nematodes of food-producing livestock and have a wide margin of safety. Some of them have zero meat and milk withdrawal times.

In the United States, there are, currently, six commercially available macrocyclic lactones: Ivermectin, Eprinomectin, Moxidectin, Selamectin, Doramectin and Milbemycin. The macrocyclic lactones are not effective against trematodes and cestodes. To compensate for this, Applicants' method includes administering to the nasal pharnyx of animals, including humans, one or more avermectins/milbemycins in combination with one or more other anthelmintic drugs. In certain embodiments, Applicants' method includes administering via the nasal pharnyx ivermectin in combination with Clorsulon.

Production of avermectins from natural fermentation of *Streptomyces avermitilis* results in a mixture of eight slightly different components. They are designated A1a, A1b, A2a, A2b, B1a, B1b, B2a and B2b. Of these, only A2a, B1a and B2a are produced in significant amounts during fermentation. The B1 homologs are the most potent and also have the broadest spectrum of activity, at least among the nematodes.

The a and b homologs have almost identical activities and because a is produced in much greater amounts than b, the terminology used to describe the avermectins is often shortened to omit separate reference to the a and b homologs and the more abundant a component is the only one shown in structural drawings. This is illustrated below in reference to ivermectin.

| Ivermectin terminology | |
|---|---|
| Common description | Actual components |
| 22, 23 dihydro(xy) avermectin B1 | 22, 23 dihydro(xy) avermectin B1a (>80%) + 22, 23 dihydro(xy) avermectin B1b (<20%) |

Milbemycins result from fermentation of *Streptomyces hygroscopicus* and *Streptomyces cyaneogriseus*. They are also produced as mixtures of slightly different components similar to the avermectins.

The macrocyclic lactones appear to act by interacting with glutamate-gated chlorine channels in muscle membranes. This interaction opens these chloride channels allowing chlorine ions to pass through and alter muscle function resulting in paralysis. The specific sites of action may include not only somatic muscles but also pharyngeal muscles since experiments with ivermectin using *Haemonchus contortus* and *Trichostrongylus colubriformis* have shown more potent inhibition of pharyngeal pumping than motility. Although most of the experiments have been done with ivermectin, it is generally believed that all macrocyclic lactones will share the same mode of action.

The macrocyclic lactones are expensive. Nevertheless, these macrocyclic lactones have gained wide acceptance by veterinarians, horse owners, farmers and the dog and cat owning public. Prior art methods of administering ivermectin vary considerably with respect to effective delivery and ease of use. Comparing subcutaneous injection of ivermectin with topical application of ivermectin, administration by injection realizes a cost efficiency with a lower time efficiency.

The following example is presented to further illustrate to persons skilled in the art how to make and use the invention and to identify presently preferred embodiments thereof. This example is not intended, however, as a limitation upon the scope of the invention, which is defined only by the appended claims.

EXAMPLE

To study the dose/response efficacy of nasal administration of macrocyclic lactone parasicides, three (3) beef steers of mixed breeding were used to evaluate three treatments. These three treatments were:

| | |
|---|---|
| Treatment 1 | 500 milligrams of ivermectin in 5 ml propylene glycol; 1 ml of mixture administered to nasal pharnyx at level of about 248 $\mu$g/kg body weight; |

-continued

| | |
|---|---|
| Treatment 2 | 1,000 milligrams of ivermectin in 5 ml propylene glycol; 1 ml of mixture administered to nasal pharnyx at level of about 409 µg/kg body weight; |
| Treatment 3 | 1,500 milligrams of ivermectin in 5 ml propylene glycol; 1 ml of mixture administered to nasal pharnyx at level of about 872 µg/kg body weight; |

Treatments were applied and cattle were bled via jugular venipuncture at 0, 6, 24, 48, and 96 hours post-dosing.

TABLE I

| | 0 Hours | 6 Hours | 24 Hours | 48 Hours | 96 Hours |
|---|---|---|---|---|---|
| Treatment 1 | 0.19 | 5.87 | 15.24 | 11.22 | 7.58 |
| Treatment 2 | 0.21 | 6.58 | 24.48 | 19.71 | 13.88 |
| Treatment 3 | 0.22 | 22.51 | 40.79 | 30.53 | 19.38 |

Table I recites serum levels of ivermectin, in nanograms per milliliter, for the three treatments recited above at 0, 6, 24, 48, and 96 hours post dosing by nasal administration. Each treatment included delivering a 1 ml mixture comprising ivermectin and propylene glycol to the nasal pharnyx of the animal.

Referring now to FIG. 1, graph 100 recites the data of Table I. Curve 110 shows the serum concentration of ivermectin over time resulting from Treatment 1. Nasal administration of ivermectin in propylene glycol at a dosage of about 248 micrograms per kilogram body weight gave a maximum serum level $C_{MAX(1)}$ of about 15 nanograms of ivermectin per ml of blood at about 24 hours post-dosing.

Curve 120 shows the serum concentration of ivermectin over time resulting from Treatment 2. Nasal administration of ivermectin in propylene glycol at a dosage of about 409 micrograms per kilogram body weight gave a maximum serum level $C_{MAX(2)}$ of about 24 nanograms of ivermectin per ml of blood at about 24 hours post-dosing.

Curve 130 shows the serum concentration of ivermectin over time resulting from Treatment 3. Nasal administration of ivermectin in propylene glycol at a dosage of about 872 micrograms per kilogram body weight gave a maximum serum level $C_{MAX(3)}$ of about 41 nanograms of ivermectin per ml of blood at about 24 hours post-dosing.

In a publication entitled "Comparison of pharmokinetic profiles of doramectin and ivermectin pour-on formulations in cattle," Veterinary Parasitology, 81, 47–55 (1999), Gayrard, Alvinerie, and Toutain report that the clinical efficacy of parasiticides, including ivermectin, depends upon the parasites' systemic exposure to the parasiticide. Id. at 54. Gayrard, Alvinerie, and Toutain further report that serum levels of ivermectin in cattle in excess of 2 ng/ml are sufficient to protect the animal against reinfestation of most parasites. Id.

As those skilled in the art will appreciate, when an animal is infested with one or more parasite species, a rapid increase in serum level of ivermectin is advantageous to rid the animal of those one or more parasites. In addition, prolonged serum levels exceeding about 2 ng $ml^{-1}$ are advantageous to prevent reinfestation. Table I and FIG. 1 clearly show that Applicants' method produced the maximum serum level of ivermectin, $C_{MAX}$, at about 24 hours post dosing for all three treatments discussed above. Table I and FIG. 1 further show that Applicants' method results in serum levels of ivermectin exceeding 2 ng $ml^{-1}$ for well in excess of 96 hours.

Levels 140 and 150 comprise $C_{MAX}$ blood levels obtained using prior art methods, namely by administering ivermectin by subcutaneous injection and topical application, respectively. Gayrard, Alvinerie, and Toutain administered ivermectin topically at a dosage of 500 micrograms per kilogram body weight. This article reports a $C_{MAX}$ for ivermectin of 12.2 ng/ml which occurred 3.4 days after administration. Referring again to FIG. 1, Level 150 on graph 100 graphically depicts the $C_{MAX}$ reported by Gayrard, Alvinerie, and Toutain.

As curve 110 shows, Applicants' nasal administration of ivermectin at a dosing of about 248 micrograms per kilogram in Treatment 1 resulted in a $C_{MAX(1)}$ of greater than 15 ng/ml which occurred about 1 day after administration. Thus, comparing Applicants' nasal administration of ivermectin with a prior art topical administration, Applicants' method using half the dosage of ivermectin nevertheless achieves a higher maximum serum level in about one third of the time. Those skilled in the art will appreciate that Applicants' nasal delivery of ivermectin achieves a higher $C_{MAX}$ at a faster rate. Those skilled in the art will appreciate that Applicants' method is clearly more cost-effective and time-effective than prior art topical administration.

In an article entitled "Comparing Pharmacokinetics of IVOMEC (ivermectin) 1% Injection and DECTOMAX (doramectin) 1% Injectable in Cattle," Merial Veterinary Bulletin, TSB-8-98031FTB (1998), Joanne Bicknese reports a $C_{MAX}$ serum level of ivermectin of about 30 ng/ml after injection of a dose of about 200 micrograms of ivermectin per kilogram of bodyweight. Bicknese further reports that the $C_{MAX}$ level occurred about 3–4 days after administration. Level 140 on graph 100 graphically depicts Bicknese's reported $C_{MAX}$.

As those skilled in the art will appreciate, a parenteral ivermectin formulation must necessarily be sterilized prior to administration. Because ivermectin is subject to decomposition at autoclave temperatures, a parenteral ivermectin formulation must be sterilized using other techniques. U.S. Pat. No. 4,853,372 teaches sterilizing a parenteral ivermectin formulation using membrane filtration.

Comparing Applicants' nasal administration of ivermectin with prior art parenteral administration methods, Applicants' nasal administration gives a $C_{MAX}$ in a shorter time period, and does not require that a sterile ivermectin formulation be prepared, does not require that the ivermectin formulation be packaged using aseptic methods, and does not require that the ivermectin formulation be administered using sterile techniques. In addition, Applicants' nasal administration does not include the risk that a needle may inadvertently remain in the animal after administration. Therefore, those skilled in the art will appreciate that Applicants' nasal administration of ivermectin is at the least more time-efficient than prior art parenteral administration, and is likely also more cost-efficient.

While the preferred embodiments of the present invention have been illustrated in detail, it should be apparent that modifications and adaptations to those embodiments may occur to one skilled in the art without departing from the scope of the present invention as set forth in the following claims.

We claim:

1. A method to treat an animal infested with one or more parasite species with a parasiticide comprising the steps of:

preparing a formulation consisting of said parasiticide and propylene glycol;

delivering a therapeutically effective amount of said formulation to the animal's nasal pharynx.

2. The method of claim 1, wherein said parasiticide comprises ivermectin.

3. The method of claim 2, wherein said ivermectin is administered to said animal at a dosage of about 250 micrograms per kilogram body weight.

4. The method of claim 2, wherein said ivermectin is administered to said animal at a dosage of about 400 micrograms per kilogram body weight.

5. The method of claim 2, wherein said ivermectin is administered to said animal at a dosage of about 870 micrograms per kilogram body weight.

6. A method to increase blood levels of a macrocyclic lactone parasiticide, comprising the steps of:

preparing a formulation consisting of said parasiticide and propylene glycol;

administering said formulation to said animal via the nasal pharynx.

7. The method of claim 6, wherein said macrocyclic lactone parasiticide comprises an avermectin.

8. The method of claim 7, wherein said avermectin comprises ivermectin.

9. The method of claim 8, wherein said mixture of said ivermectin and said propylene glycol is not sterilized.

10. The method of claim 9, further comprising the steps of:

mixing about 500 milligrams of ivermectin in about 5 ml of propylene glycol; and administering about 1 ml of said mixture to the nasal pharynx of said animal.

11. The method of claim 9, further comprising the steps of:

mixing about 1,000 milligrams of ivermectin in about 5 ml of propylene glycol; and administering about 1 ml of said mixture to the nasal pharynx of said animal.

12. The method of claim 9, further comprising the steps of:

mixing about 1,500 milligrams of ivermectin in about 5 ml of propylene glycol; and administering about 1 ml of said mixture to the nasal pharynx of said animal.

13. A method to treat an animal infested with one or more parasite species with a parasiticide, comprising the steps of:

preparing a formulation consisting of ivermectin and propylene glycol;

administering said ivermectin to the animal's nasal pharynx at a dosage of about 250 micrograms per kilogram body weight, wherein the maximum serum level off ivermectin occurs about 24 hours after said nasal administration, and wherein said maximum serum level is about 15 ng $ml^{-1}$.

* * * * *